(12) United States Patent
Parker et al.

(10) Patent No.: US 8,996,128 B2
(45) Date of Patent: Mar. 31, 2015

(54) COUPLINGS FOR IMPLANTED LEADS AND EXTERNAL STIMULATORS, AND ASSOCIATED SYSTEMS AND METHODS

(71) Applicant: Nevro Corporation, Menlo Park, CA (US)

(72) Inventors: Jon Parker, San Jose, CA (US); Andre B. Walker, Monte Sereno, CA (US)

(73) Assignee: Nevro Corporation, Menlo Park, CA (US)

( * ) Notice: Subject to any disclaimer, the term of this patent is extended or adjusted under 35 U.S.C. 154(b) by 100 days.

(21) Appl. No.: 13/935,294

(22) Filed: Jul. 3, 2013

(65) Prior Publication Data

US 2013/0325092 A1 Dec. 5, 2013

Related U.S. Application Data

(63) Continuation of application No. 12/562,892, filed on Sep. 18, 2009, now abandoned.

(51) Int. Cl.
*A61N 1/00* (2006.01)
*A61N 1/05* (2006.01)
(Continued)

(52) U.S. Cl.
CPC ............ *A61N 1/0553* (2013.01); *A61N 1/0551* (2013.01); *A61N 1/36017* (2013.01);
(Continued)

(58) Field of Classification Search
CPC ... A61N 1/375; A61N 1/3752; A61N 1/0551; A61N 1/0553; A61N 1/36021; A61N 1/36017; A61N 1/04; A61N 1/048; A61N 1/0488; H01R 13/5224

USPC .................. 607/115, 117–119, 122
See application file for complete search history.

(56) References Cited

U.S. PATENT DOCUMENTS 4,211,462 A 7/1980 Wolfthal
5,052,375 A 10/1991 Stark et al.
(Continued)

OTHER PUBLICATIONS

International Search Report and Written Opinion, International Application No. PCT/US10/49376, Applicant: Nevro Corporation, European Patent Office, mailed May 26, 2011, 10 pages.
(Continued)

*Primary Examiner* — Niketa Patel
*Assistant Examiner* — William Levicky
(74) *Attorney, Agent, or Firm* — Perkins Coie LLP (57) ABSTRACT

Couplings for implanted leads and external stimulators, and associated systems and methods are disclosed. A system in accordance with a particular embodiment includes a cable assembly that in turn includes an electrical cable having a proximal end and a distal end. A first connector is attached to the cable toward the proximal end and has a plurality of first connector contacts positioned to releasably connect to an external patient device. A second connector is attached by the cable toward the distal end, and includes a first portion and a second portion pivotably connected to the first portion. The first portion has a slot elongated along a slot axis and positioned to receive an implantable patient signal delivery element axially along the slot axis. The second portion has a plurality of second connector contacts positioned to releasably, electrically contact the signal delivery element when the signal delivery element is positioned within the slot and the first and second portions are placed in a secured position. At least one of the first and second portions is pivotable relative to the other between the secured position and an unsecured position.

20 Claims, 7 Drawing Sheets

(51) Int. Cl.
   *A61N 1/36* (2006.01)
   *A61N 1/375* (2006.01)
   *A61N 1/04* (2006.01)

(52) U.S. Cl.
   CPC .......... *A61N1/36021* (2013.01); *A61N 1/3752* (2013.01); *A61N 1/0488* (2013.01); *A61N 1/04* (2013.01); *A61N 1/375* (2013.01); *A61N 1/00* (2013.01); *A61N 1/048* (2013.01)
   USPC .......... 607/115; 607/117; 607/118; 607/119; 607/122

(56) References Cited

U.S. PATENT DOCUMENTS

| | | |
|---|---|---|
| 5,241,957 A | 9/1993 | Camps et al. |
| 5,261,395 A | 11/1993 | Oleen et al. |
| 5,354,326 A | 10/1994 | Comben et al. |
| 5,557,210 A | 9/1996 | Cappa et al. |
| 5,560,358 A | 10/1996 | Arnold et al. |
| 5,931,861 A | 8/1999 | Werner et al. |
| 6,039,685 A | 3/2000 | Bushek |
| 6,192,278 B1 | 2/2001 | Werner |
| 6,325,778 B1 | 12/2001 | Zadno-Azizi et al. |
| 6,397,108 B1 | 5/2002 | Camps et al. |
| 6,671,534 B2 | 12/2003 | Putz |
| 7,425,142 B1 | 9/2008 | Putz |
| 2003/0062048 A1 | 4/2003 | Gradon et al. |
| 2003/0228805 A1 | 12/2003 | Schwarz |
| 2004/0034392 A1 | 2/2004 | Spadgenske |
| 2004/0230268 A1 | 11/2004 | Huff et al. |
| 2006/0030918 A1 | 2/2006 | Chinn et al. |
| 2006/0148326 A1 | 7/2006 | Putz |
| 2006/0253160 A1 | 11/2006 | Benditt et al. |
| 2009/0112272 A1 | 4/2009 | Schleicher et al. |
| 2009/0132016 A1 | 5/2009 | Putz |
| 2009/0233491 A1 | 9/2009 | Barker et al. |
| 2010/0274336 A1 | 10/2010 | Nguyen-Stella et al. |
| 2010/0305670 A1 | 12/2010 | Hall et al. |
| 2011/0071593 A1 | 3/2011 | Parker |

OTHER PUBLICATIONS

Supplementary European Search Report for European Patent Application No. 10817939.1, Applicant: Nevro Corporation, mailed May 7, 2013, 7 pages.

COUPLINGS FOR IMPLANTED LEADS AND EXTERNAL STIMULATORS, AND ASSOCIATED SYSTEMS AND METHODS

CROSS-REFERENCE TO RELATED APPLICATIONS

The present application is a continuation of U.S. patent application Ser. No. 12/562,892, filed on Sep. 18, 2009 and incorporated herein by reference. To the extent the foregoing application and/or any other materials incorporated herein by reference conflict with the present disclosure, the present disclosure controls.

TECHNICAL FIELD

The present disclosure is directed generally to couplings for implanted leads and external stimulators, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. In pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation.

One problem associated with existing stimulation systems and methods is that the practitioner may not initially implant the SCS lead in the optimal position. Accordingly, practitioners typically make small adjustments to the position of the implanted lead while the patient is in the operating room. The practitioner then applies stimulation to the lead via an external stimulator, which is temporarily attached to the lead while the lead still extends out of the patient's body. This process is repeated until the practitioner determines the position of the lead that is expected to produce the best patient result. The patient and practitioner can also use the external stimulator during a post-operative trial period, to optimize the characteristics of the applied signal before an implantable pulse generator is connected to the lead and implanted beneath the patient's skin.

To facilitate the foregoing process of alternately providing stimulation to the patient and moving the implanted portion of the lead, manufacturers have developed cables with releasable connectors. Accordingly, the practitioner can connect the cable to the external stimulator and the lead, apply the stimulation, then disconnect the cable, move the lead, and reconnect the cable with the lead in the new position. As noted above, this process can be repeated, as needed, until the desired lead location is obtained.

One drawback with the foregoing approach is that it may be difficult for the practitioner to repeatedly manipulate the connector that attaches the cable to the lead, while still maintaining control over the position of the lead. Another drawback is that the connectors, which are outside the patient's body, may be awkward and/or cumbersome for the patient during the post-operative trial period. Accordingly, there remains a need for improved techniques and systems for releasably connecting implanted patient leads to external stimulation devices.

DETAILED DESCRIPTION

Overview

Aspects of the present disclosure are directed generally to couplings that may be used to connect implanted leads or other implanted signal delivery elements, with external stimulators and/or other devices positioned external to a patient. Several aspects of the disclosure are described in the context of a spinal cord stimulation (SCS) system for purposes of illustration. In other embodiments, the disclosed systems and methods may be used in the context of other patient treatment and/or patient diagnostic systems. Several embodiments of representative systems and methods are described below with reference to FIGS. 1-8C. A person skilled in the relevant art will understand, however, that the disclosure may have additional embodiments, and/or that aspects of the disclosure may be practiced without several of the details of the embodiments described below.

A patient treatment system in accordance with a particular embodiment includes a cable assembly that in turn includes an electrical cable having a proximal end and a distal end, with a first connector attached to the cable toward the proximal end, and a second connector attached to the cable toward the distal end. The first connector can include a plurality of first connector contacts positioned to releasably connect to an external patient device, for example, an external stimulator. The second connector can include a first portion and a second portion pivotably connected to the first portion. The first portion can have a slot elongated along a slot axis and positioned to receive an implantable patient signal delivery element axially along the slot axis. The second portion can have a plurality of second connector contacts positioned to releasably, electrically contact the signal delivery element when the signal delivery element is positioned within the slot and the first and second portions are placed in a secured position. The first and second portions are pivotable relative to each other between the secured position and an unsecured position.

A representative method for operating a patient treatment system can include implanting an implantable signal delivery element in a patient, and positioning a cable proximate to connection contacts of the implantable signal delivery device. The cable can include a proximal end with a first connector having first connector contacts, and a distal end with a second connector having first and second portions. The method can further include sliding the connection contacts of the signal delivery element axially into a slot carried by the second portion of the second connector. The method can still further include pivoting at least one of the first and second portions relative to the other to electrically connect the connection contacts of the signal delivery device with second connector contacts carried by the second portion of the second connector. The first connector can be releasably connected to an external patient device, for example, an external patient stimulator. As will be described further below, aspects of the foregoing systems and associated methods can allow the practitioner to manipulate the cable assembly connectors with only one hand, and/or can improve patient comfort while the cable assembly is connected to an implanted lead or other signal delivery element.

Representative Systems and Methods

Figure 1:
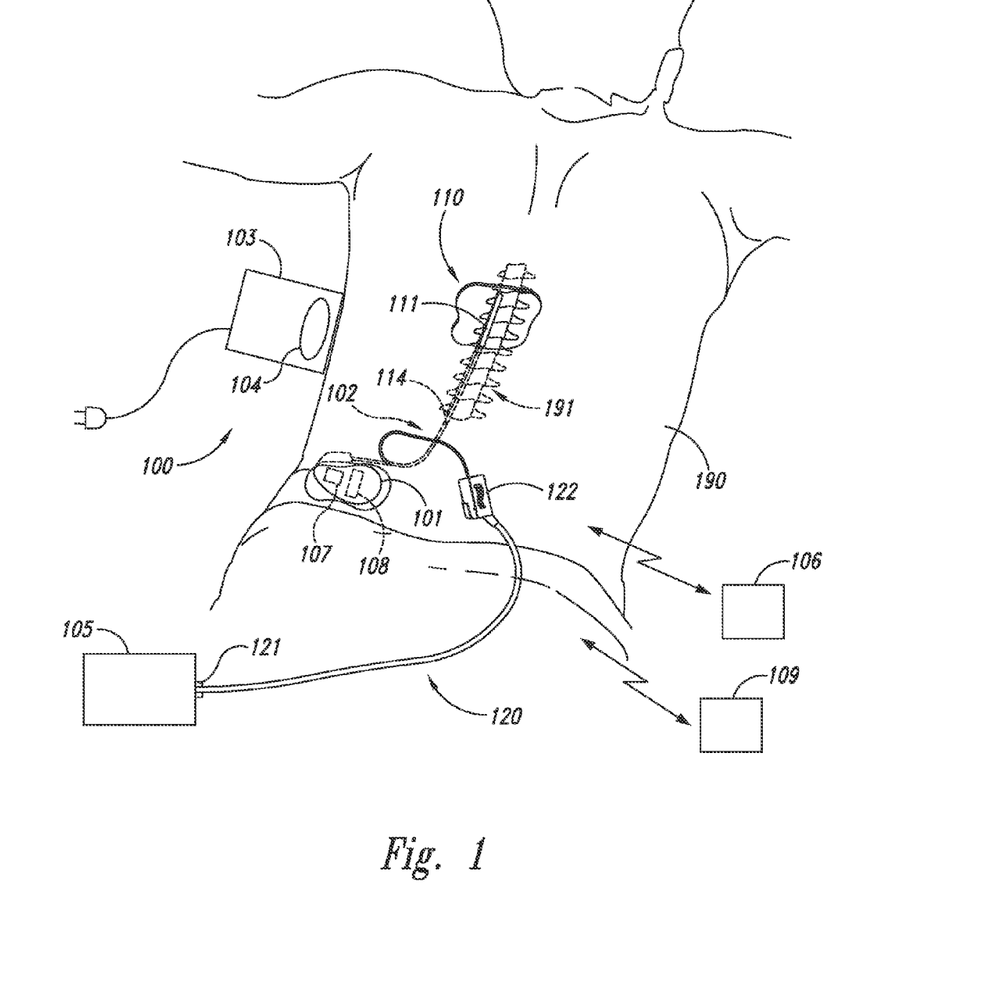
FIG. 1 is a partially schematic illustration of an implantable spinal cord stimulation system positioned at the spine to deliver a therapeutic signal in accordance with an embodiment of the present disclosure.

FIG. 1 schematically illustrates a representative treatment system 100 for providing relief from chronic pain and/or other conditions, arranged relative to the general anatomy of a patient's spinal cord 191. The system 100 can include a pulse generator 101, which may be implanted subcutaneously within a patient 190 and coupled to a signal delivery element 110. In a representative example, the signal delivery element 110 includes a lead or lead body 111 that carries features or elements for delivering therapy to the patient 190 after implantation. The pulse generator 101 can be connected directly to the lead 111, or it can be coupled to the lead 111 via a communication link 102 (e.g., an extension). Accordingly, the lead 111 can include a terminal section that is releasably connected to an extension at a break 114 (shown schematically in FIG. 1). This allows a single type of terminal section to be used with patients of different body types (e.g., different heights). As used herein, the terms lead and lead body include any of a number of suitable substrates and/or support members that carry devices for providing therapy signals to the patient 190. For example, the lead 111 can include one or more electrodes or electrical contacts that direct electrical signals into the patient's tissue, such as to provide for patient relief. In other embodiments, the signal delivery element 110 can include devices other than a lead body (e.g., a paddle) that also direct electrical signals and/or other types of signals to the patient 190.

The pulse generator 101 can transmit signals to the signal delivery element 110 that up-regulate (e.g., stimulate or excite) and/or down-regulate (e.g., block or suppress) target nerves. As used herein, and unless otherwise noted, the terms "stimulate" and "stimulation" refer generally to signals that have either type of effect on the target nerves. The pulse generator 101 can include a machine-readable (e.g., computer-readable) medium containing instructions for generating and transmitting suitable therapy signals. The pulse generator 101 and/or other elements of the system 100 can include one or more processors 107, memories 108 and/or input/output devices. Accordingly, the process of providing stimulation signals and executing other associated functions can be performed by computer-executable instructions contained on computer-readable media, e.g., at the processor(s) 107 and/or memory(s) 108. The pulse generator 101 can include multiple portions, elements, and/or subsystems (e.g., for directing signals in accordance with multiple signal delivery parameters), housed in a single housing, as shown in FIG. 1, or in multiple housings.

In some embodiments, the pulse generator 101 can obtain power to generate the therapy signals from an external power source 103. The external power source 103 can transmit power to the implanted pulse generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

In another embodiment, the pulse generator 101 can obtain the power to generate therapy signals from an internal power source, in addition to or in lieu of the external power source 103. For example, the implanted pulse generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

In many cases, an external programmer 105 (e.g., a trial stimulator) is coupled to the signal delivery element 110 during an initial implant procedure, prior to implanting the pulse generator 101. For example, a practitioner (e.g., a physician and/or a company representative) can use the external programmer 105 to vary the stimulation parameters provided to the signal delivery element 110 in real time, and select optimal or particularly efficacious parameters. These parameters can include the position of the signal delivery element 110, as well as the characteristics of the electrical signals provided to the signal delivery element 110. In a typical process, the practitioner uses a cable assembly 120 to temporarily connect the external programmer 105 to the signal delivery device 110. The cable assembly 120 can accordingly include a first connector 121 that is releasably connected to the external programmer 105, and a second connector 122 that is releasably connected to the signal delivery element 110. The practitioner can test the efficacy of the signal delivery element 110 in an initial position. The practitioner can then disconnect the cable assembly 120, reposition the signal delivery element 110, and reapply the electrical stimulation. This process can be performed iteratively until the practitioner obtains the desired position for the signal delivery device 110. Optionally, the practitioner may move the partially implanted signal delivery element 110 without disconnecting the cable assembly 120. In either embodiment, the practitioner will connect and disconnect the cable assembly 120 at least once during the process. Further details of features that facilitate this process are described below with reference to FIGS. 3-8C.

After the position of the signal delivery element 110 and appropriate signal delivery parameters are established using the external programmer 105, the patient 190 can receive therapy via signals generated by the external programmer 105, generally for a limited period of time. In a representative application, the patient 190 receives such therapy for a one-week trial period. During this time, the patient wears the cable assembly 120 and the external programmer 105 outside the body. Assuming the trial therapy is effective or shows the promise of being effective, the practitioner then replaces the external programmer 105 with the implanted pulse generator 101, and programs the pulse generator 101 with parameters selected based on the experience gained during the trial period. Optionally, the practitioner can also replace the signal delivery element 110. Once the implantable pulse generator 101 has been positioned within the patient 190, the signal delivery parameters provided by the pulse generator 101 can still be updated remotely via a wireless physician's programmer (e.g., a physician's remote) 109 and/or a wireless patient programmer 106 (e.g., a patient remote). Generally, the patient 190 has control over fewer parameters than does the practitioner. For example, the capability of the patient programmer 106 may be limited to starting and/or stopping the pulse generator 101, and/or adjusting stimulation amplitude.

Figure 2:
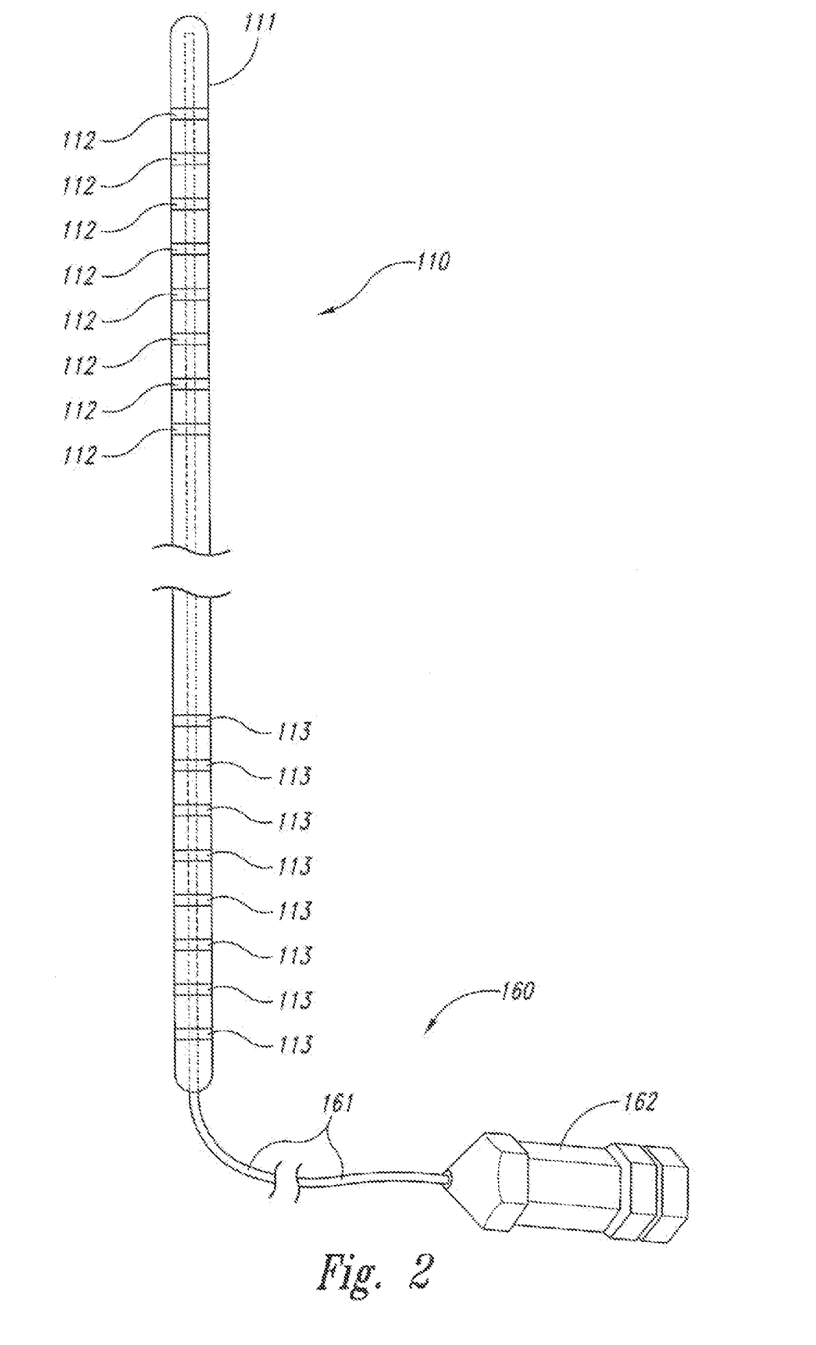
FIG. 2 is a partially schematic illustration of a lead having stimulation contacts and externally positioned connector contacts, suitable for providing stimulation in accordance with representative methods of present disclosure.

FIG. 2 is a partially schematic illustration of a representative signal delivery device 110 that includes a lead 111 having a plurality of stimulation contacts 112 toward the distal end that are implanted within the patient. The lead 111 includes internal wires that extend between the stimulation contacts 112 at the distal end and connection contacts 113 positioned at the proximal end. During the trial period, the connection contacts 113 extend outside the patient's body and are connected to an external stimulator. After the trial period is complete, the connection contacts 113 are connected to the implanted pulse generator 101 (FIG. 1). During implantation, a stylet 160 or other delivery device is temporarily connected to the lead 111 to support the lead 111 as it is positioned within the patient. Accordingly, the stylet 160 can include a shaft 161 and a handle 162. The shaft 161 is generally flexible, but more rigid than the lead 111 to allow the practitioner to insert the lead 111 and control its position during implantation.

Figure 3:
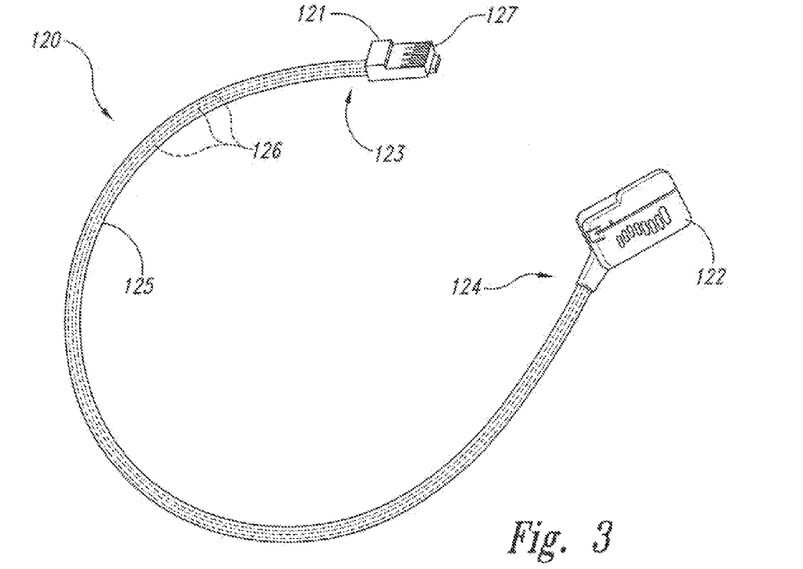
FIG. 3 is a partially schematic, isometric illustration of a cable assembly suitable for releasably coupling a patient lead or other signal delivery element to an external stimulator or other device in accordance with an embodiment of the disclosure.

FIG. 3 is a partially schematic, isometric illustration of a cable assembly 120 that can be releasably connected to the signal delivery element 110 shown in FIG. 2. The cable assembly 120 includes a cable 125 carrying a plurality of electrical conductors 126. A first connector 121 having first connector contacts 127 is positioned toward a proximal end 123, with the first connector contacts 127 electrically connected to the electrical conductors 126. A second connector 122 is connected to the cable 125 toward a distal end 124 and includes second connector contacts, also connected to the electrical conductors 126 and described later with reference to FIG. 5.

Figure 4:
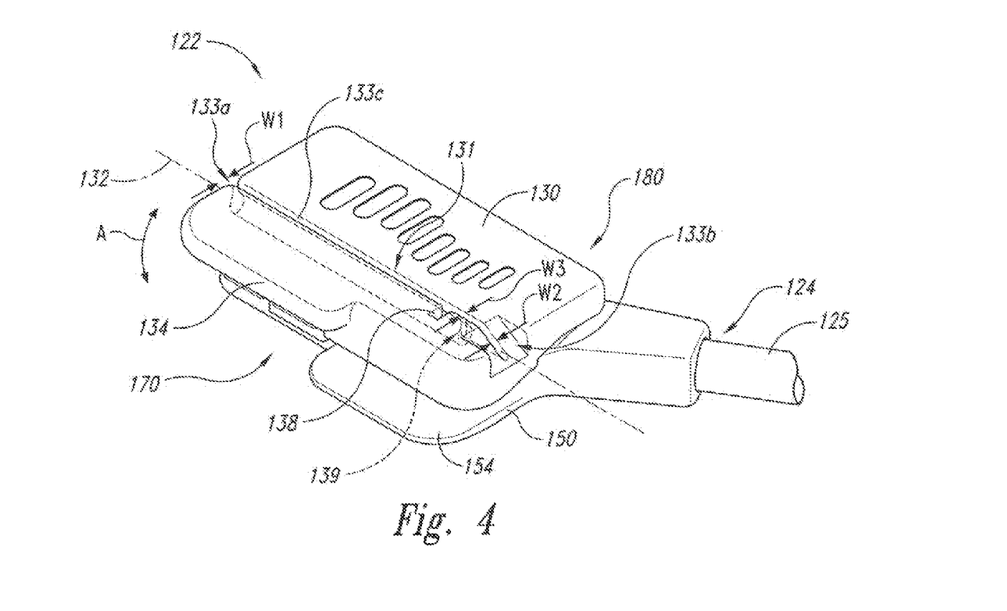
FIG. 4 is a partially schematic, isometric illustration of a connector configured in accordance with an embodiment of the disclosure.

FIG. 4 is a partially schematic, isometric illustration of the distal end 124 of the cable 125 and the second connector 122. The bulk of the second connector 122 can be formed from ABS or another suitable biocompatible plastic or other material. In a particular aspect of this embodiment, the second connector 122 includes a first portion, e.g., a first housing portion 130 pivotably connected to a second portion, e.g., a second housing portion 150 via a hinge 180. Accordingly, at least one of the first housing portion 130 and the second housing portion 150 can be pivoted relative to the other (as indicated by arrow A) between a secured position and an unsecured position. The second connector 122 can have a corresponding secured configuration and unsecured configuration, respectively. The first housing portion 130 includes a slot 131 elongated along a slot axis 132. The slot 131 can include a first opening 133a positioned toward one end of the slot axis 132, a second opening 133b positioned toward the opposite end of the slot axis 132, and a third opening 133c extending along the slot axis 132 between the first opening 133a and the second opening 133b. The slot 131 is positioned to receive a lead or other signal delivery device, and an associated stylet. Accordingly, the first opening 133a can have a first width W1 sized to receive the lead, the second opening 133b can have a smaller second width W2 sized to receive the stylet shaft, and the third opening 133c can have a third width W3, also sized to receive the stylet shaft.

The first housing portion 130 can include a lead stop 139 within the slot 131 to stop the axial progress of the lead and to align the lead with electrical contacts in the second housing portion. In a particular embodiment, the lead stop 139 is a surface facing toward the first opening 133a, and located at a point where the cross-sectional shape of the slot 131 changes from one that accommodates both the lead 111 and the stylet shaft, to one that accommodates the stylet shaft only. An alignment indicator 138 provides the practitioner with visual confirmation that the lead is properly aligned. The first housing portion 130 can include a first tab 134 and the second housing portion 150 can include a second tab 154, both of which facilitate pivoting the two housing portions relative to each other. For example, the two tabs 134, 154 can be offset from each other in a direction generally parallel to the slot axis 132 to operate in a manner similar to that of a change purse. A latch 170 can hold the housing portions 130, 150 in a secured position when the lead or other signal delivery element is positioned in the slot 131.

Figure 5:
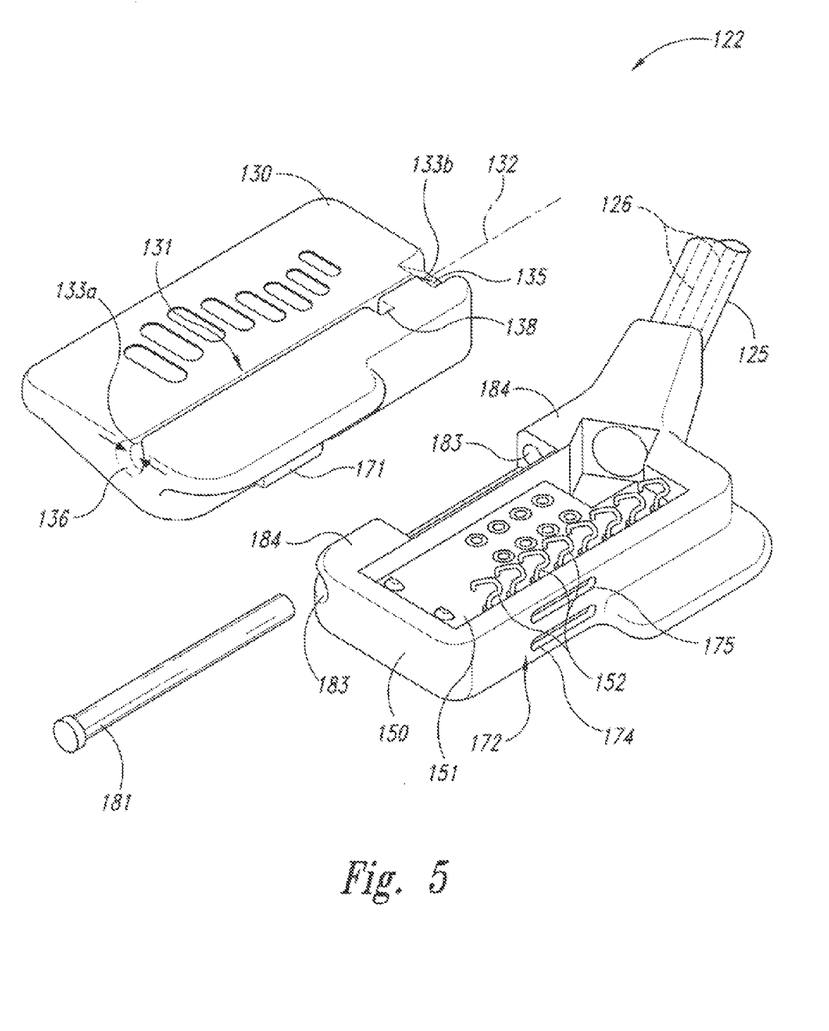
FIG. 5 is an exploded, partially schematic illustration of an embodiment of the connector shown in FIG. 4.

FIG. 5 is a partially schematic, partially exploded isometric illustration of an embodiment of the second connector 122 shown in FIG. 4. As shown in FIG. 5, the second housing portion 150 includes two outer hinge elements 184, each having second pin apertures 183 that slidably receive a corresponding hinge pin 181. The hinge pin 181 also passes through a corresponding inner hinge element described further below with reference to FIG. 6. The second housing portion 150 can carry a support member 151 that in turn carries second connector contacts 152. The second connector contacts 152 are electrically connected to the electrical conductors 126 carried by the cable 125. The second connector contacts 152 project upwardly toward the first housing portion 130 so as to releasably engage with a lead placed in the slot 131 of the first housing portion 130. As shown in FIG. 5, the slot 131 can include a funnel surface 136 at the first opening 133a to facilitate sliding a lead into the slot 131 along the slot axis 132. A ramp surface 135 at the second opening 133b can facilitate movement of the stylet handle 162 (FIG. 2) relative to the slot 131. As is also shown in FIG. 5, the first housing portion 130 can include a first latch element 171 that releasably engages with a corresponding second latch element 172 of the second housing portion 150. The second latch element 172 can include a latching slot 174 that receives the first latch element 171 when the second connector 122 is secured. The second housing portion 150 can also include a pivot stop slot 175 that also receives the first latch element 171 in the unsecured position to prevent the first housing portion 130 from over-rotating away from the second housing portion 150. The stop slot 175 can also inhibit the practitioner from inadvertently placing the second connector 122 in the secured configuration.

Figure 6:
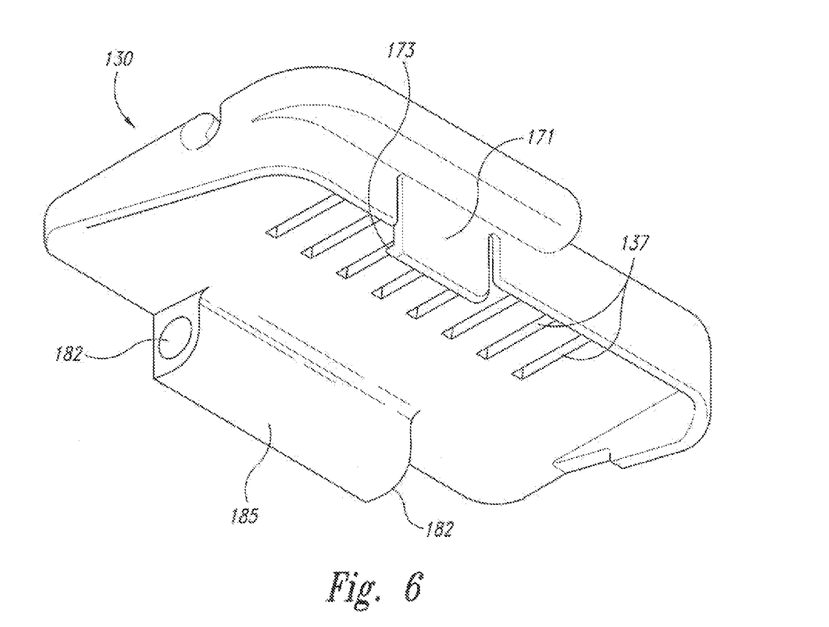
FIG. 6 is a partially schematic, upwardly looking isometric view of a first housing portion of an embodiment of the connector shown in FIGS. 4 and 5.

FIG. 6 is an isometric, upward-looking view toward the inner surface of the first housing portion 130. This view illustrates the inner hinge element 185 of the first housing portion 130, which has two first pin apertures 182 that slidably receive the hinge pin 181 described above with reference to FIG. 5. The first housing portion 130 further includes contact apertures 137. The contact apertures 137 can be blind slots that receive the upwardly projecting portions of the second connector contacts 152 shown in FIG. 5. The first latch element 171 shown in FIG. 6 can include a projection 173 that is releasably received in the latching slot 174 shown in FIG. 5 when the second connector 122 is secured, and in the pivot stop slot 175 (also shown in FIG. 5) when the second connector 122 is unsecured.

Figure 7A:
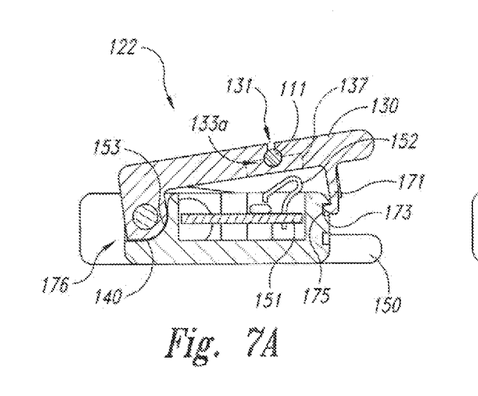
FIGS. 7A and 7B illustrate a connector shown in an unsecured position and a secured position, respectively, in accordance with an embodiment of the disclosure.
Figure 7B:
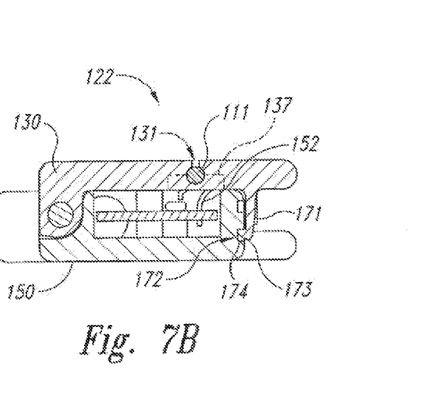

FIGS. 7A and 7B are cross-sectional illustrations of the second connector 122 shown in the unsecured position (FIG. 7A) and the secured position (FIG. 7B). In FIG. 7A, the first housing portion 130 is pivoted away from the second housing portion 150 to the unsecured position. A lead 111 is inserted into the first opening 133a, but does not yet contact the second connector contacts 152 carried by the support member 151 of the second housing portion 150. In this position, the first housing portion 130 can be prevented from rotating too far away from the second housing portion 150 because the projection 173 of the first latch element 171 is received in the pivot stop slot 175 of the second housing portion 150. In a particular embodiment, the pivot stop slot 175 can be positioned to prevent the first and second housing portions 130, 150 from rotating by more than about 5° away from each other. In other embodiments, the amount of rotation can be greater, for example, less than 45°, or less than 90°. The particular angular value can be selected so that the connection contacts of the lead just disengage from the second connector contacts 152 when the second connector 122 is in the unsecured position. In any of these embodiments, it is expected that limiting the relative rotation of the two housing portions 130, 150 can facilitate the user's ability to secure and/or unsecure the second connector 122, for example, by facilitating single handed operation of the second connector 122.

In one embodiment, the pivot stop slot 175 alone prevents the housing portions 130, 150 from over-rotating relative to each other. In another embodiment, shown in FIG. 7A, this function can be supplemented by another pivot stop 176 formed by the respective shapes of a downward-facing first surface 140 of the first housing portion 130, and an upward-facing second surface 153 of the second housing portion 150. For example, the first and second surfaces 130, 153 can be shaped to rotate smoothly relative to each other up to the selected maximum pivot angle, and to mechanically interfere with each other at angles beyond the maximum pivot angle. In a particular example, the first surface can be cylindrical (e.g., radially symmetric about the pivot axis) over only the part of its circumference that facilitates smooth rotation. In still another embodiment, this arrangement can replace the similar function provided by the pivot stop slot 175.

FIG. 7B illustrates the second connector 122 in the secured position. In this position, the first and second housing portions 130, 150 have been pivoted toward each other, so that the lead 111 engages with the second connector contacts 152. At least a portion of each second connector contact 152 can be received in a corresponding contact aperture 137 so that the second connector contacts 152 do not interfere with moving the housing portions 130, 150 toward each other to the secured position. In the secured position, the first latch element 171 (and in particular, the projection 173) can be secured to the second latch element 172, e.g., received in the latching slot 174. In this position, the second connector 122 can remain in the secured position until positively acted upon by the practitioner.

Figure 8A:
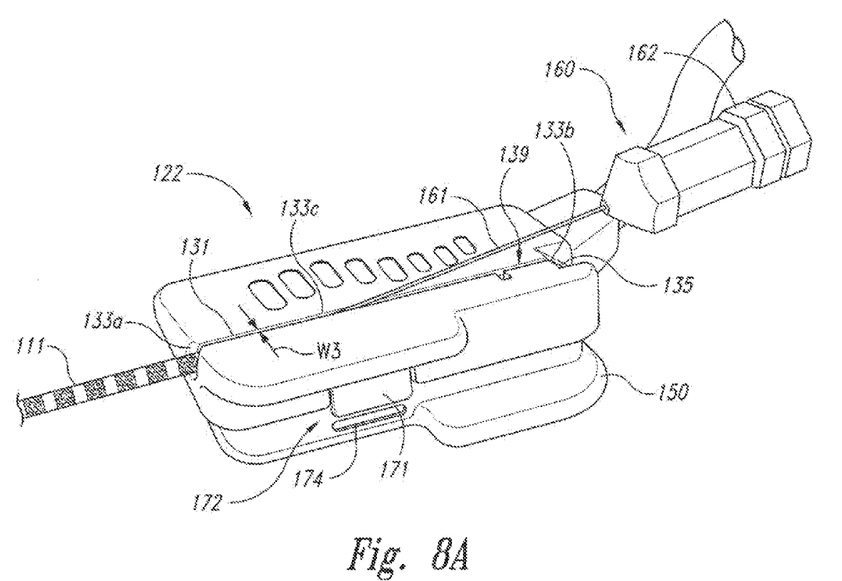
FIGS. 8A-8C illustrate a method for operating a cable system in accordance with an embodiment of the disclosure.
Figure 8B:
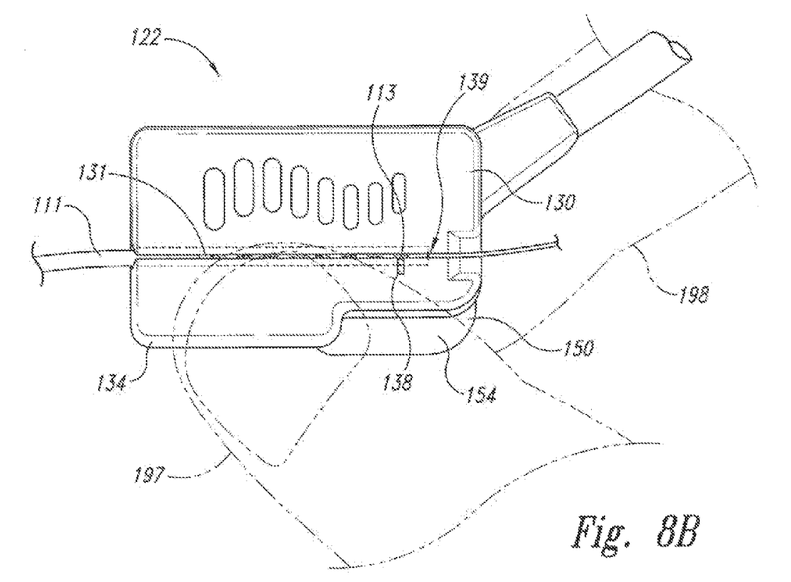
Figure 8C:
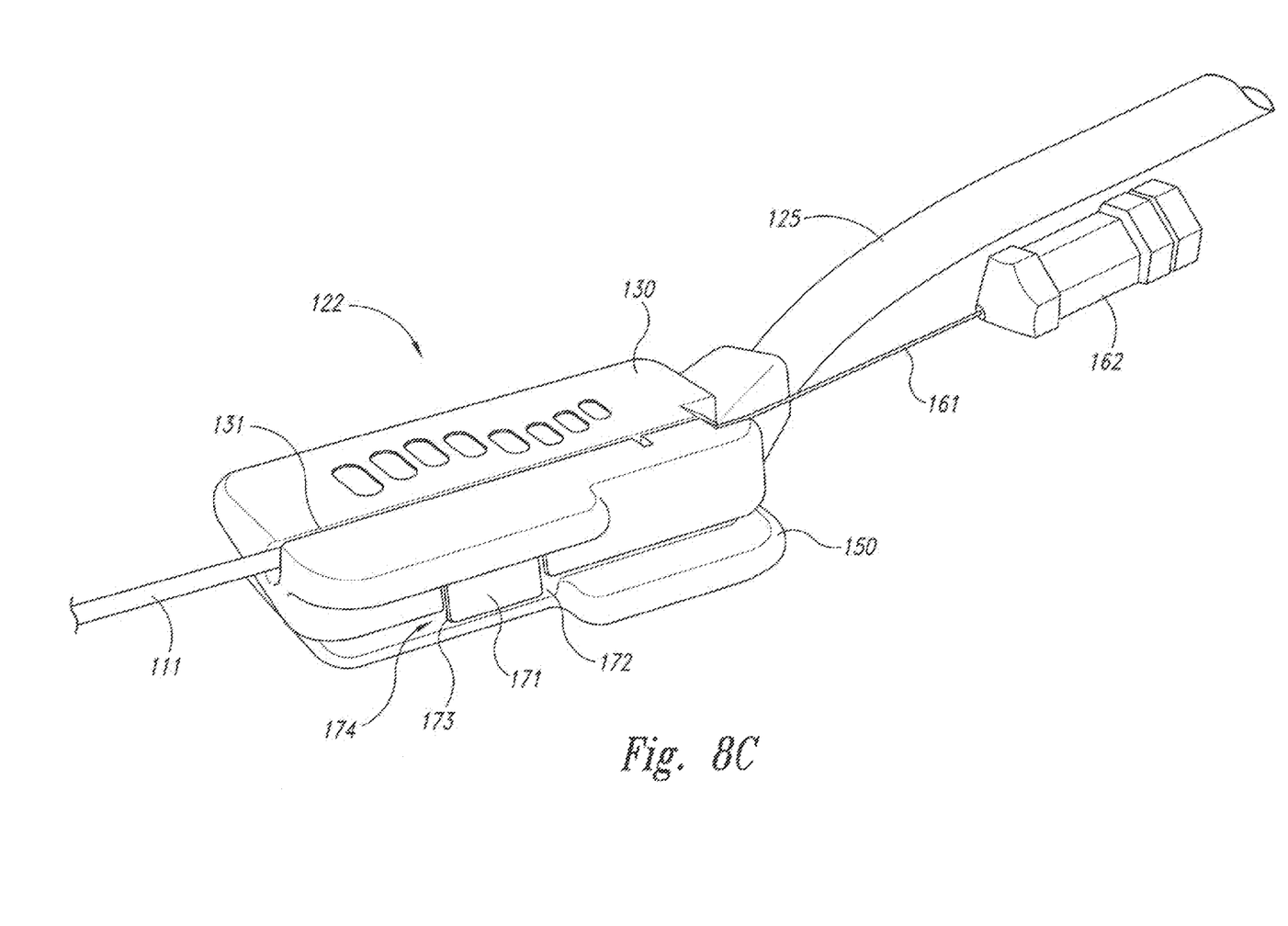

FIGS. 8A-8C are schematic illustrations of the second connector 122 illustrating a sequence of operation steps in accordance with an embodiment of the disclosure. In FIG. 8A, the second connector 122 is in the unsecured configuration, with the first latch element 171 disengaged from the second latch element 172. One feature of this arrangement is that the practitioner can easily discern that the second connector 122 is in the unsecured configuration by noting the visibly exposed latching slot 174 (e.g., the inner surfaces of the latching slot 174). With the second connector 122 in the unsecured configuration, the practitioner can slide the lead 111 axially into the first opening 133a of the slot 131. In a particular embodiment, the practitioner slides the lead 111 axially into the slot 131 until the distal end of the lead 111 engages with the lead stop 139 located within the slot 131. In another aspect of the illustrated embodiment, the stylet 160 can optionally be pre-inserted into the lead 111 before the lead 111 is placed in the slot 131. In this case, the third opening 133c can receive the stylet shaft 161 without interfering with the practitioner's axial insertion of the lead 111. In particular, the width W3 of the third opening 133c is wide enough to allow the stylet shaft 161 to move downwardly into the slot 131, yet narrow enough to prevent the lead 111 from inadvertently being moved upwardly out of the slot 131. The ramp surface 135 at the second opening 133b can allow the stylet handle 162 to pivot upwardly and downwardly relative to the first housing portion 130, without catching on the upper edge of the first housing portion 130.

FIG. 8B is a top view of the second connector 122, illustrating the lead 111 after it has been pushed as far as possible into the slot 131, so as to engage with the lead stop 139. In this position, at least one of the connection contacts 113 (e.g., the first in a row of connection contacts) is visible through the slot 131, and is aligned with the alignment indicator 138. Accordingly, the practitioner can receive visual confirmation that the lead 111 is properly positioned in the slot 131. With the lead 111 in this position, the practitioner can move at least one of the first housing portion 130 and the second housing portion 150 relative to each other to the secured position using only a single hand. For example, the practitioner can engage the first closure tab 134 with a first part of the hand (e.g., the forefinger 198) and engage the second closure tab 154 with a second part of the hand (e.g., the thumb 197) and press the two housing portions 130, 150 together, providing both a pivoting force to move the housing portions toward each other, and a reaction force to hold the second connector 122 in position, all with one hand.

As is also shown in FIG. 8B, the second connector 122 can have a relatively small size. For example, the second connector can have an overall length of about 33.4 millimeters, an overall width of about 21.6 millimeters, and an overall thickness of 8.7 millimeters. The exposed surface area is accordingly about 7.2 square centimeters, which is significantly smaller than existing connectors sized to receive a lead having eight connection contacts 113. In other embodiments, the footprint of the second connector 122 can be even smaller.

FIG. 8C illustrates the second connector 122 in the secured configuration. In this configuration, the projection 173 of the first latch element 171 is received in the latching slot 174 of the second latch element 172. Accordingly, the latching slot 174 is no longer visible to the practitioner, thus confirming that the second connector 122 is in the secured configuration. The practitioner can also hear and/or feel a click or snap as the projection 173 is received in the latching slot 174. With the second connector 122 in the secured configuration, the practitioner can apply signals to the lead 111, and, based on feedback (e.g., patient feedback), can adjust the position of the lead as desired.

One feature of at least some of the foregoing embodiments described above with reference to FIGS. 1-8C is that the lead 111 or other signal delivery element 110 can be introduced into the second connector 122 by sliding it axially into and along the slot 131, without at the same time engaging the connection contacts 113 with the second connector contacts 152. As a result, the lead 111 can be moved into the slot 131 easily, with low frictional resistance, and with a reduced likelihood for dislodging or otherwise moving the lead 111 relative to the patient. When the practitioner does engage the connection contacts 113 with the second connector contacts 152, the practitioner can do so with only one hand, allowing the practitioner to hold the lead 111 in place relative to the patient with the other hand. For example, the practitioner's hand can provide both the moving force and the reaction force imparted to the second connector 122, which reduces the likelihood for the second connector 122 to slip out of the practitioner's grasp.

Another feature of at least some of the foregoing embodiments is that the angle between the two housing portions 130, 150 is relatively small when the second connector 122 is in the unsecured configuration. For example, the angle can be less than 90°, less than 45° or less than 5°. An advantage of this arrangement is that it facilitates the practitioner's ability to secure and unsecure the second connector 122 with one hand. For example, when the angle has a value less than 90°, the practitioner can avoid placing forces on the housing portions 130, 150 that have a vector component which tends to unsecure the second connector 122 when the practitioner is attempting to secure the second connector 122. In addition, the amount of hand movement required to secure and/or unsecure the second connector 122 is relatively small, which decreases the likelihood that the practitioner will fumble with the second connector 122.

Still another feature of at least some of the foregoing embodiments is that the second connector 122 has a relatively small footprint (e.g., projected area, generally normal to the major surfaces of the first or second housing portions 130, 150). An expected advantage of this feature is that the small size makes the second connector 122 easier to manipulate. Another expected advantage of this feature is that the second connector will be less bulky and therefore more comfortable for the patient to wear during the trial period.

From the foregoing, it will be appreciated that specific embodiments of the disclosure have been described herein for purposes of illustration, but that various modifications may be made without deviating from the disclosure. For example, in other embodiments, the second connector can include other arrangements that limit or prohibit over-rotating one housing portion relative to the other. In still further embodiments, the second connector can include other arrangements for securing one housing portion relative to the other, and/or for halting the axial movement of the lead or other signal delivery element positioned in the second connector. In yet further embodiments, the practitioner can leave the second connector attached to the implanted signal delivery element while the signal delivery element is repositioned, rather than disconnecting and reconnecting the connector with each new signal delivery element position.

Certain aspects of the disclosure described in the context of particular embodiments may be combined or eliminated in other embodiments. For example, in certain embodiments, the signal delivery element can have features different than those shown in FIG. 2, and/or can be supported by a device other than a stylet. Further, while advantages associated with certain embodiments have been described in the context of those embodiments, other embodiments may also exhibit such advantages and not all embodiments need necessarily exhibit such advantages to fall within the scope of the present disclosure. Accordingly, the disclosure can encompass other embodiments not expressly described or shown herein.

We claim:

1. A patient treatment system for delivering therapy to a patient, comprising:
   a signal delivery element having a lead with connection contacts along a proximal portion thereof; and
   a cable assembly including
      an electrical cable having a proximal end and a distal end,
      a first connector attached to the proximal end of the cable, the first connector having a plurality of first connector contacts positioned to releasably connect to an external patient device, and
      a second connector attached to the distal end of the cable, the second connector including
         a first housing portion having a first latch element and a longitudinally extending slot that is configured to slidably receive the proximal portion of the lead, and
         a second housing portion having a second latch element and a plurality of second connector contacts positioned to electrically contact the connection contacts of the lead,
         wherein the first and second housing portions are pivotably connected to each other such that the second connector is pivotable between a partially opened, unsecured position in which the first and second latch elements are in a first latched configuration with the connection contacts of the lead being disengaged from the second connector contacts, and a closed, secured position in which the first and second latch elements are in a second latched configuration with the connection contacts of the lead being engaged with the second connector contacts.

2. The system of claim 1, wherein the first latch element includes a projection and the second latch element includes first and second slots configured to receive the projection.

3. The system of claim 2, wherein in the first latched configuration the projection is received within the first slot such that the second connector is in the partially opened, unsecured position.

4. The system of claim 3, wherein in the second latched configuration the projection is received within the second slot such that the second connector is in the closed, secured position.

5. The system of claim 3, wherein in the first latched configuration a maximum opening between the first and second housing portions of the second connector in the partially opened, unsecured position is less than about 90°.

6. The system of claim 3, wherein in the first latched configuration a maximum opening between the first and second housing portions of the second connector in the partially opened, unsecured position is less than about 45°.

7. The system of claim 3, wherein in the first latched configuration a maximum opening between the first and second housing portions of the second connector in the partially opened, unsecured position is less than about 5°.

8. The system of claim 1, wherein the longitudinally extending slot of the first housing portion has first, second and third openings, the first opening being at a first end of the slot and having a first width transverse to a longitudinal axis of the slot, the second opening being at a second end of the slot and having a second width transverse to the longitudinal axis of the slot, and the third opening extending in parallel with the slot from the first opening to the second opening and having a third width transverse to the longitudinal axis of the slot with the third width being less than at least one of the first and second widths.

9. The system of claim 8, wherein the lead of the signal delivery element has a diameter less than the first width and the signal delivery element further includes a stylet having a diameter less than the third width.

10. The system of claim 1, wherein the second housing portion includes a support member in which the second connector contacts are disposed so as to align with and extend into corresponding contact apertures of the first housing portion when the second connector is in the closed, secured position.

11. The system of claim 1, wherein the second housing portion includes a support member in which the connector contacts are disposed so as to align with and extend into corresponding contact apertures of the first housing portion when the connector is in the closed, secured position.

12. A patient treatment system for delivering therapy to a patient, comprising:
an implantable patient lead with a plurality of connection contacts along a proximal portion thereof; and
a cable assembly including
an electrical cable, and
a connector attached to the cable for connecting to the lead, the connector including
a first housing portion having a first latch element and a longitudinally extending slot that is configured to slidably receive the lead, and
a second housing portion hinged to the first housing portion such that the first and second housing portions are pivotably connected, the second housing portion having a second latch element and a plurality of connector contacts positioned to electrically contact the connection contacts of the lead,
wherein the at least part of the connector is movable between an unsecured position in which the first and second latch elements are in a first latched configuration and a secured position in which the first and second latch elements are in a second latched configuration.

13. The system of claim 12, wherein when the connector is in the unsecured position the connector contacts of the second housing portion are disengaged from the connection contacts of the lead.

14. The system of claim 13, wherein when the connector is in the secured position the connector contacts of the second housing portion are engaged with the connection contacts of the lead.

15. The system of claim 12, wherein the first latch element includes a projection and the second latch element includes first and second slots configured to receive the projection.

16. The system of claim 15, wherein in the first latched configuration the projection is received within the first slot such that the connector is in the unsecured position.

17. The system of claim 16, wherein in the second latched configuration the projection is received within the second slot such that the connector is in the secured position.

18. The system of claim 16, wherein in the first latched configuration a maximum opening between the first and second housing portions of the connector in the unsecured position is less than about 90°.

19. The system of claim 16, wherein in the first latched configuration a maximum opening between the first and second housing portions of the connector in the unsecured position is less than about 45°.

20. The system of claim 16, wherein in the first latched configuration a maximum opening between the first and second housing portions of the connector in the unsecured position is less than about 5°.

* * * * *